United States Patent [19]

Labuda et al.

[11] Patent Number: 5,279,950
[45] Date of Patent: * Jan. 18, 1994

[54] BIOCONVERSION PROCESS FOR THE PRODUCTION OF VANILLIN

[75] Inventors: Ivica M. Labuda, Ossining; Steven K. Goers, Yonkers; Kathleen A. Keon, Mohegan Lake, all of N.Y.

[73] Assignee: Kraft General Foods, Inc., Northfield, Ill.

[ * ] Notice: The portion of the term of this patent subsequent to Jul. 7, 2009 has been disclaimed.

[21] Appl. No.: 906,083

[22] Filed: Jun. 29, 1992

Related U.S. Application Data

[63] Continuation-in-part of Ser. No. 708,543, May 31, 1991, Pat. No. 5,128,253.

[51] Int. Cl.$^5$ .......................... C12P 7/24; C12R 1/15; C12R 1/40; C12R 1/685
[52] U.S. Cl. ..................... 435/147; 435/41; 435/156; 435/240.4; 435/240.45; 435/240.46; 435/822; 435/843; 435/877; 435/911; 435/917
[58] Field of Search ............... 435/147, 156, 827, 843, 435/877, 911, 917, 240.4, 240.45, 240.46, 240.48, 41

[56] References Cited

U.S. PATENT DOCUMENTS

| | | | |
|---|---|---|---|
| 5,057,424 | 10/1991 | Knuth et al. | 435/240.48 |
| 5,068,184 | 11/1991 | Knuth et al. | 435/41 |
| 5,128,253 | 7/1992 | Labuda et al. | 435/147 |

*Primary Examiner*—Herbert J. Lilling
*Attorney, Agent, or Firm*—Thomas A. Marcoux; Linn I. Grim; Thomas R. Savoie

[57] ABSTRACT

The present invention is directed to a process for the production of vanillin through the bioconversion of a vanillin precursor with a tissue culture of undifferentiated callus cells derived from a vanilla plant and/or enzymes obtained therefrom in the presence of a water soluble sulfhydryl compound and optionally, also in the presence of an assimilable carbon source.

10 Claims, No Drawings

BIOCONVERSION PROCESS FOR THE PRODUCTION OF VANILLIN

This application is a continuation-in-part application of our copending application, U.S. Ser. No. 708,543 which was filed on May 31, 1991 now U.S. Pat. No. 5,128,253, issue date of Jul. 7, 1992.

TECHNICAL FIELD

This invention relates to a method for producing vanillin from natural vanillin precursors by a bioconversion process and more specifically, to a process for increasing the yield of vanillin when vanillin precursors are treated with a ferulic acid degrading microorganism in the presence of a sulfhydryl compound.

BACKGROUND ART

Vanilla is extracted from the cured pods of the flowers of the vanilla vine, a member of the orchid family. During the curing process, a large number of flavor compounds are formed which impart to the extract the pleasing aroma and well balanced organoleptic properties characteristic of vanilla. While vanilla is highly prized for use in flavoring a broad array of foodstuffs, its use is restricted by high cost stemming from the complex, low yielding methods associated with its manufacture. Vanillin (3-methoxy-4-hydroxybenzaldehyde) is one of the principle components responsible for the characteristic aroma and flavor of vanilla extract. Synthetic vanillin, most often produced by the treatment of sulfite waste liquors from paper mills, is typically used as a low cost substitute for vanilla and indeed may even be present as an adulterant in vanilla extract. Because of its origin and method of manufacture, vanillin derived from sulfite waste liquor is not considered to be a natural food component nor may it be so labeled in the U.S. A process for the production of natural vanillin via the bioconversion of natural vanillin precursors by a low cost process would therefore have great value and utility.

It is well known that vanillin is formed in small quantities from aromatic compounds known to be precursors in the biosynthesis of lignin (see Rahouti, Mohammed, et al., Appln. Environ. Microbiol., 55:2391-8, Sep., 1989; Tadasa, K., Agric. Biol. Chem. 41:925-9, 1977; Sutherland, J. B. et al., Can. J. Microb., 29:1253-7, 1983). Trans-ferulic is a common precursor in the biosynthesis of lignin as well as a lignin degradation product. The metabolism of ferulic acid by soil microorganisms typically leads to the production of vanillin but the vanillin so formed is further converted to vanillic acid and/or vanillyl alcohol which in turn are typically transformed to other degradation products such as protocatechuic acid, guaiacol, hydroquinones, catechol, ring-cleavage products, etc. Thus, it is generally recognized that vanillin is an intermediate in the overall scheme for the biodegradation of ferulic acid and ferulic acid precursors so that only small amounts of vanillin accumulate when ferulic acid is biodegraded by soil microorganisms. There are a large number of references which report on the metabolism of aromatic compounds by soil microorganisms (e.g., *Pullularia pullulans Fusarium sp., Aspergillus niger, Bacillus sp., Pseudomonas sp., Nocardia sp.*, see Borneman, W. S. et al., Appl. Microbiol. Biotechnol. 33:354-51, 1990; Eggeling, L. et al., Arch. Microbiol. 126:141-8, 1980) but none stress the potential for using such microorganisms for vanillin synthesis because vanillin accumulates only small quantities as an intermediate product.

U.S. Pat. No. 5,057,424 to Knuth and Sahai teaches callus cells which are independent of and unattached to differentiated plant tissue which are derived from plant tissue. The callus cells are capable of growth in cell culture without forming differentiated cell structures. The vanilla plant callus cells secrete vanillin and related vanillin flavor components into the culture medium in which they are cultured. The patent specification identifies three principal variables in the liquid culture medium which can be adjusted to improve the yield of vanillin and related components. These variables are (a) nutrient, (b) plant hormones, and (c) vanilla component precursors. The inventors report that experiments leading to the Knuth et al. invention suggest that phenylalanine and ferulic acid, two metabolic precursors of vanillin, produced little enhancement in vanillin production by the callus cell culture. The copending application to Knuth and Sahai which issued as U.S. Pat. No. 5,068,184 discloses a process to produce a vanilla flavor composition by suspending vanilla-plant callus cells in tissue culture under conditions that promote the secretion of vanilla flavor components by the cells into the culture medium. Both Knuth and Sahai patents identified above are herein incorporated by reference into the present application.

DISCLOSURE OF THE INVENTION

It has been discovered that vanillin accumulation via microbial treatment of ferulic acid and related compounds can be materially increased through the incorporation of a sulfhydryl compound such as, for example, dithiothreitol and dithioerythritol, into the bioconversion mixture. Sulfhydryl compounds are well known protective agents for enzymes as well as for oxidation sensitive substances in general so that the metabolic pathway for the transformation of vanillin precursors by ferulic acid degrading microorganisms may be altered by the inclusion of a sulfhydryl compound with the result that vanillin accumulation is enhanced. While we do not wish to be held to any specific theory regarding mechanism, it is believed that the presence of the sulfhydryl compound affects one or more of the enzymatic steps involved in the formation of vanillin in the overall biodegradation pathway so that the vanillin concentration in the transformation mixture is increased when compared to like mixtures without the added sulfhydryl compound.

It has also been discovered that the bioconversion of vanillin precursors according to the present invention produces other compounds which impart pleasant flavor notes to the bioconversion mixture and contribute in a positive manner to the sensory character of the mixture increasing its value as a flavorant for foods.

According to the invention, there is provided a method for the production of vanillin by the treatment of a vanillin precursor with a ferulic acid degrading microorganism in the presence of a sulfhydryl compound. More specifically, a vanillin precursor such as ferulic acid, eugenol, 4-vinylguaiacol and the like, is treated with the cells of a ferulic acid degrading microorganism capable of forming vanillin from ferulic acid in the presence of one or more sulfhydryl compounds plus a metabolizable carbon source under conditions suitable for biotransformation.

In carrying out the invention, the microorganism is cultured in the substantial absence of a vanillin precursor under conditions of time, temperature, pH, nutrient type, nutrient concentration and aeration to provide a quantity of viable cells or mycelium which is then isolated and used in a subsequent bioconversion (vanillin production) step. In carrying out the bioconversion step, the isolated cells are added to an aqueous mixture comprising the vanillin precursor, the sulfhydryl compound plus any buffer or other ingredients needed to maintain cell viability to form a bioconversion mixture, and the mixture is incubated at a temperature and for a time sufficient to effect substantial conversion of the vanillin precursor to vanillin. In the preferred embodiment, an assimilable carbon source suitable for promoting growth and/or maintenance of the cells is also present in the bioconversion mixture.

An additional discovery has been made, specifically that in carrying out the process patented by Knuth et al. in U.S. Pat. Nos. 5,057,424 and 5,068,184 increased levels of vanillin and related vanillin flavor components can be produced from callus cells when a vanillin precursor and a sulfhydryl compound are incorporated into the culture medium. The specific vanillin precursor compounds and sulfhydryl compounds are the same compounds that exhibit improvement in the bioconversion process which utilizes a ferulic acid degrading microorganism. Alternatively, instead of utilizing callus cells the process can incorporate enzymes which are obtained from the callus cells.

BEST MODE FOR CARRYING OUT THE INVENTION

As a source of ferulic acid degrading microorganism, any of the common types cited in the literature capable of the degradation of ferulic acid may be used provided the microorganism is able to effect the degradation through a pathway wherein vanillin is an intermediate. Thus, it is envisaged that many types of fungi, bacteria and yeasts will work in the present invention as a large number of microorganisms with this capability are known. For the purposes of this invention, "ferulic acid degrading microorganism" will hereinafter refer to those microorganisms capable of growth on trans-ferulic acid to 4-substituted guaiacols by a pathway wherein vanillin is an intermediate. Illustrative of this (but not limiting) are *Paecilomyces varioti* and *Pestaloti palmarum* which convert ferulic acid to vanillin via 4-vinylguaiacol (see Rahouti, M. et al. above) as do *Pseudomonas cepacia* (see Andreoni, V., et al., Syst. Appl. Microbiol., 5:299-304, 1980), and *Fusarium solani* (see Nazareth, S. et al., Can. J. Microbiol., 32:494-7, 1986). *Polyporous versicolor* (Ishikawa, H., et al., Arch. Biochem. Biophys., 100:140-9, 1963), and *Pseudomonas acidovorans* (Toms, A., et al., Biochemistry 9:337-43, 1970) are also known to transform ferulic acid to vanillin via elimination of side chain carbons. A *Corynebacteriumg sp.* is capable of transforming eugenol to vanillin via ferulic acid (Tadasa, K., Agric. Biol. Chem., 41(6):925-9, 1977).

Yet other microorganisms are known, may be isolated, discovered, or otherwise developed through selection, mutation, and/or genetic transformation processes with the characteristic and necessary capability for the transformation of ferulic acid to vanillin and methods for their isolation, selection and development are well known to the skilled practitioner.

Suitability of microorganisms for use in the present invention may be determined by simple test procedures using well known methods. For example, the microorganism to be tested may be propagated in a rich medium (e.g., LB-medium, Bacto-tryptone yeast extract medium, nutrient medium and the like) at a pH, temperature and under aeration conditions commonly used for propagation of the microorganism. The cells are harvested by centrifugation or filtration and are washed with the identical sterile medium containing no assimilable carbon source. The washed cells are suspended in minimal medium (e.g., Mandels medium, MCGC medium, YNB medium) containing 0.1% trans-ferulic acid plus 0.1% glucose, and the mixture is incubated with or without aeration at 30 degrees C. Aliquots of supernatant are withdrawn from the incubation mixture at 12 hour intervals and are analyzed by HPLC for vanillin, the presence of which is indicative of ferulic acid degradation via the vanillin pathway. Vanillic acid and/or 4-vinylguaiacol are also commonly found as ferulic acid degradation products, usually at concentrations exceeding that of vanillin.

Preferred ferulic acid degrading microorganisms for the purposes of the present invention are from the genus Pseudomonas, Corynebacterium, Trichoderma, Rhodotorula and Aspergillus. Most preferred are organisms such as *Aspergillus niger, Rhodotorula glutinis* and *Corynebacterium glutamicum*.

The ferulic acid degrading microorganism may be cultured in a number of ways in order to provide cells suitable for the subsequent bioconversion step. Culturing should be carried out under conditions yielding viable cells in all cases if such cells are to be used for the subsequent bioconversion step. Since the microorganisms applicable for the bioconversion step vary broadly (yeasts, bacteria and fungi), culturing conditions must, of course be adjusted to the specific requirements of each species and these conditions are well known and documented. Any of the art known methods for growing cells of ferulic acid degrading microorganisms may be used to produce the cells utilizable in the subsequent bioconversion step of the present invention. However, submerged fermentation using pure culture techniques are preferred. In some cases, it has been found desirable to control the growth stage of the culture used for the bioconversion if optimum results are to be obtained. For example, it is preferable to use early stationary phase cells (ca. 24 hours old) when bioconversions with *Rhodotorula glutinis* are carried out. In contrast, late stationary phase cells are preferable when A. niger is used. The optimum growth stage needed to establish maximum vanillin production in a subsequent bioconversion step is, of course, easily determined by simple test procedures.

A number of vanillin precursors are applicable for use in the present invention. All are found to be derivatives of guaiacol substituted at the 4 position as follows:

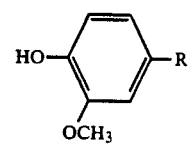

In the above formula, the R group may comprise (but is not limited to) the following structures:

| Structure of R Group | Common Name of 4-Substituted Guaiacol |
|---|---|
| —CH=CH—COOH | Ferulic acid (both cis- & trans isomers) |
| —CH=CH$_2$ | 4-vinylguaiacol |
| —CH$_2$—CH=CH$_2$ | Eugenol |
| —CH=CH—CH$_2$OH | Coniferyl alcohol |
| —CH=CH—CHO | Coniferyl aldehyde |
| —CH=CH—CH$_2$OH | Vanillyl alcohol |
| —COOH | Vanillic acid |
| —CH=CH—CH$_3$ | Isoeugenol |
| —CH$_2$—CH——CH$_2$ <br> \\ / <br> O | Eugenol oxide |
| —CH$_2$—CH(OH)—CH$_2$OH | Eugenol diol |

Ferulic acid, eugenol, coniferyl alcohol and 4-vinylguaiacol are preferred precursors, especially when obtained from natural sources. Most preferred is trans-ferulic acid. While vanillin precursors obtained from natural sources are preferred (for example, cereal grains are rich sources of ferulic acid moieties), like compounds obtained by wholly synthetic routes will, of course, work equally well in the invention.

Any of a number of sulfhydryl compounds are applicable in the present invention so long as they are water soluble to the extent of at least 10 mM and are not toxic to the ferulic acid degrading microorganism. Preferred are polyhydric sulfhydryl compounds having the following general formula:

$$HS—CH_2—(CH(OH))_n—CH_2—SH$$

where n in the above formula can vary from 1 to 4. Thus, the preferred sulfhydryl compounds are dithiols. Most preferred are a dithiothreitol (D,L-threo-1,4-dimercapto-2,3-butanediol) and dithioerythritol (D,L-erythro-1, 4-dimercapto-2,3-butanediol). Other applicable sulfhydryl compounds include beta-mercaptoethanol, mercaptoacetic acid and the like. Such are less preferred owing to their volatility, offensive odor and necessity for complete removal if the bioconversion mixture is to be used for flavoring foods. Also utilizable are sulfhydryl compounds such as sulfur containing amino acids commonly metabolize by microorganisms, i.e. cysteine and derivatives of sulfur containing amino acids, i.e. glutathione. However, it is necessary to use such under conditions that minimize their degradation by the ferulic acid degrading microorganism as for example when readily metabolized carbon sources such as glucose are present in excess in the bioconversion mixture. Preferably, the sulfhydryl compound is used in the bioconversion mixture at a concentration ranging from about 1 mM to about 100 mM and most preferably from about 5 mM to about 20 mM.

In order to carry out the bioconversion step, an aqueous solution containing the vanillin precursor and the sulfhydryl compound is contacted with the ferulic acid degrading microorganism to form a bioconversion mixture which is maintained under conditions of pH, temperature, and agitation necessary to promote the conversion of the precursor to vanillin. It is highly preferred that the bioconversion mixture also contain other substances necessary to promote the viability of the microorganism such as mineral salts, buffers, cofactors, nutrient substances and the like. The general requirements for the maintenance of viability of ferulic acid degrading microorganisms are well known. Specific requirements for maintaining the viability of specific microorganisms are also well documented in the literature or other otherwise easily determined by the skilled microbiologist. Preferably, the solution used for forming the bioconversion mixture consists of a minimal medium such as Mandels medium or MCGC medium (see below) to which is added the vanillin precursor and the sulfhydryl compound. The mixture is then held at a pH and temperature necessary to promote vanillin production. Preferred pH is between about pH 3 and about pH 7 and preferred temperature is between about 20 degrees C., about 40 degrees C. Further, it is highly preferred that the bioconversion mixture contain a source of assimilable carbon for the ferulic acid degrading microorganism, for example, glucose, sucrose, fructose, maltose and the like. Use of an assimilable carbon source in the bioconversion mixture materially increases the yield of vanillin. The most preferred carbon source is glucose.

Although conditions for maintaining cell viability must be maintained throughout the bioconversion step, it is not necessary that active cell growth occurs. It is in fact preferable that the ferulic acid degrading cells be in stationary phase for this step. It is also preferable that reducing conditions be maintained in the mixture during the bioconversion step. While absolute anaerobic conditions are not a requirement, it is preferable that incorporation of oxygen into the bioconversion mixture through stirring or agitation be minimized to avoid oxidation of the sulfhydryl compound and vanillin, particularly when pH is greater than about 6.0. Oxygen may also be excluded, of course, by conducting the bioconversion step under inert atmosphere, e.g., under a nitrogen blanket.

Owing to the general toxicity displayed by many of the vanillin precursors towards microorganisms, it may be necessary to limit the concentration of such in the bioconversion mixture. It is therefore preferred that the concentration of vanillin precursor be limited to the range between about 0.025% and 1.0% at any given time during biotransformation. This is particularly true for those precursors which tend to be fat soluble (e.g., eugenol) as opposed to those with greater water solubility and lower toxicity such as for example, ferulic acid. Multiple additions of precursor may be made throughout the course of the bioconversion step in order to replace precursor as it is converted to vanillin. Likewise, multiple additions of sulfhydryl compound may be made to the bioconversion mixture during the course of the bioconversion step.

Also contemplated in the invention is the use of vanillin complexing agents, adsorbants, and extractants and especially those agents with high selectivity for vanillin which may be added to or otherwise contacted with the bioconversion mixture to remove vanillin as it is formed. It is expected that use of such agents would have a twofold benefit in that the detrimental effects of excess vanillin accumulation (which is itself toxic to most microorganisms) would be avoided and degradation of vanillin through subsequent conversion to unwanted by-products could be avoided.

The following table gives information on the general effects observed when bioconversions are run with and without a polyhydric sulfhydryl compound (dithiothreitol).

| Microorganism | Vanillin Precursor | Vanillin Conc. (ug/ml) | |
|---|---|---|---|
| | | Without DTT | With DTT |
| Aspergillus niger | Ferulic Acid | 2.2 | 93.7 |
| " | Eugenol | 1.2 | 18.5 |
| Pseudomonas putida | Ferulic Acid | 0.4 | 139.4 |
| " | Eugenol | 1.2 | 4.7 |
| Corynebacterium glutamicum | Ferulic Acid | 16.2 | 115.0 |
| " | Eugenol | 3.3 | 3.8 |
| Rhodotorula glutinis | Ferulic Acid | 0.4 | 80.6 |

In general, the effect of the sulfhydryl compound in increasing vanillin accumulation during the bioconversion is clearly apparent.

The following specific examples are given to illustrate the invention. Mandels medium (Mandels, M. and Andreotti, R. E., Process Biochem. 13:6-15, 1978) contained 1.5% $KH_2PO_4$, 0.5% $(NH_4)_2SO_2$, 0.03% $CaCl_2$, 5 ppm $FeSO_4 \cdot 7H_2O$, 1.6 ppm $MnSO_4 \cdot 7H_2O$, 2 ppm $CoCl_2$, 1.4 ppm $ZnSO_4$, 0.03% urea, 0.05% $MgSO_4$ and 0.2% peptone. YNB medium contained per liter, 1.7 g yeast nitrogen base, 5 g ammonium sulfate, and 100 ug biotin, and was adjusted to pH 7.0 with NaOH. MCGC medium contained 0.6% $Na_2HPO_4$, 0.3% $KH_2PO_4$, 0.1% NaCl, 0.4% $(NH_4)_2SO_4$, 0.1% trisodium citrate, 200 ppm $MgSO_4$, 20 ppm $FeSO_4 \cdot H_2O$, 2 ppm $FeCl_3$, 0.5 ppm $ZnSO_4 \cdot 7H_2O$, 0.2 ppm $CuCl_2 \cdot 2H_2O$, 2 ppm $MnSO_4 \cdot H_2O$, 0.1 ppm $(NH_4)_6Mo_7O_{24}$, 0.2 ppm $Na_2B_4O_7 \cdot 10H_2O$, 38 ppm $CaCl_2$, 5 ppm thiamine, and the 0.5 ppm biotin.

Bioconversion mixtures were analyzed for vanillin content and for the content of other aromatic compounds by reverse phase high performance liquid chromatography using a Perkin-Elmer HS3 C18 column (Pecosphere 3×8C cartridge, C18). One-ml samples of the bioconversion mixtures were centrifuged to remove cells and 10-ul samples of supernate injected for analysis. Elution was effected with 1% aqueous acetic acid containing 10-40% methanol (linear gradient). Emerging peaks were monitored with a Perkin-Elmer multiwavelength detector (LC95 UV/VIS) at 310 nm. Components were identified by retention time and quantified by comparison with purified standard compounds.

The present invention also relates to improving the amount of vanillin and related vanillin flavor components produced from callus cells derived from vanilla plants by incorporating into the culture medium containing the callus cell tissue culture a vanillin precursor and sulfhydryl compound. The vanillin precursor and sulfhydryl compounds have been previously described. Care must be exercised to properly prepare the callus cells. Any variety of vanilla plant species, including V. fragrans, V. phaeantha, V. pompona and V. tahitensis may be used for preparation of callus cells. The preferred species are V. fragrans and V. phaeantha. The process for preparing the callus cells includes excising a tissue segment from the growing point of a vanilla plant, preferably root tips or fruit placenta tissue, culturing on a solid support in the presence of plant growth hormones and selecting those tissue segments which show callus formation. In one embodiment of the invention the callus cells produced are derived from V. fragrans and have the characteristics of ATCC No. 40354. Further details concerning the preparation of callus cells and production of vanillin by tissue culture may be found in U.S. Pat. Nos. 5,057,424 and 5,068,184, both of which are herein incorporated by reference.

When utilizing the improved invention for generating vanillin and related vanillin flavor components from callus cells derived from a vanilla plant, a bioconversion mixture is created which is made up of the following ingredients: an aqueous solution of a vanillin precursor, undifferentiated callus cells derived from a vanilla plant and/or enzymes obtained therefrom and a sulfhydryl compound. The specific vanillin precursors are derivatives of guaiacol substituted at the 4 position with the specific compounds being previously set forth in the present specification. The preferred vanillin precursors are ferulic acid, eugenol, coniferyl alcohol and 4-vinylguaiacol with ferulic acid being the most preferred. The vanillin precursor concentration should preferably vary between about 0.025% to about 1.0%. The specific sulfhydryl compounds are set forth hereinbefore with the preferred sulfhydryl compounds being DTT, DTE, glutathione and cysteine. Most preferred are DTT and DTE. Preferably, the sulfhydryl compound is used in the bioconversion mixture at a concentration ranging from about 1 mM to about 100 mM and most preferably from about 5 mM to about 20 mM.

The callus cells are maintained during vanillin production in a liquid medium preferably any conventional plant medium such as Murashige-Skoog medium which has been modified to limit the nitrogen available to the cells. The medium may also include the presence of plant hormones such as mixtures of 2,4-dichlorophenoxyacetic acid (2,4-D), benzylacetic acid (BA), naphthaleneacetic acid, 2,4,5-trichlorophenoxyacetic acid and 4-amino-3,5,6-trichloropicolinic acid used in callus cell production and growth. The vanillin precursor and sulfhydryl compound are added to the plant medium described above or any organic salt medium such as MCGC or Mandels medium and the mixture is held at a pH and temperature necessary to promote vanillin production. The preferred pH range is from about 3 to about 7 and the preferred temperature is between about 20° C. to about 40° C. It is also preferred to incorporate one of the aforementioned assimilable carbon sources, preferably glucose.

As was previously discussed, the vanillin and related vanillin flavor compounds can be removed once formed by complexing agents, adsorbants and extractants. Vanillin component production is significantly enhanced by removing vanillin and the other flavor components from the medium during production of vanillin in culture.

The following symbols are used in the examples:
FA—Ferulic Acid (trans-isomer)
EU—Eugenol
DTT—Dithiothreitol
DTE—Dithioerythritol
GSH—Glutathione
Cys—L-Cysteine

EXAMPLE 1

This example illustrates the effect of a sulfhydryl agent (dithiothreitol) in increasing the production of vanillin when vanillin precursors are treated with Pseudomonas putida cells.

Pseudomonas putida ATCC 55180 was inoculated into 50 ml of Mandels medium containing 1% glucose and was cultured at 30 degrees C. for 16 hours on a rotary shaker. The resulting cells were harvested by centrifugation and were resuspended in 10 ml of Mandels medium with no added glucose. One-ml portions of the cell suspension were added to 9-ml portions of four different reaction mixtures to form the bioconversion mixtures shown in Table 1. The mixtures were incubated at room temperature (ca. 25 degrees C.) without aeration. Vanillin concentration was determined in the mixtures at the indicated times. All bioconversion mixtures contained 0.1% glucose in addition to the added cells and reactants shown in the Table.

TABLE 1

| Mixture No. | Reactant Conc. FA (%) | EU (%) | DTT (mM) | Vanillin Conc. (ug/ml) 3 hrs | 24 hrs | 36 hrs | 1296 hrs |
|---|---|---|---|---|---|---|---|
| 1 | 0.1 | | | 0.25 | 0.10 | 0.39 | 2.90 |
| 2 | | 0.1 | | 1.24 | 0.40 | 1.40 | |
| 3 | 0.1 | | 5.0 | 31.97 | 33.00 | 32.50 | 210.00 |
| 4 | | 0.1 | 5.0 | 1.42 | 2.80 | 3.60 | |

It is clear that the dithiothreitol in the bioconversion mixtures materially increased the concentration of vanillin over those mixtures without it. The effect was particularly marked when the vanillin precursor was ferulic acid.

EXAMPLE 2

This example shows the use of Aspergillus niger cells for the bioconversion of vanillin precursors in the presence of dithiothreitol, Aspergillus niger ATCC 11414 was inoculated into 200 ml of Mandels medium containing 1% glucose and cultivated on a rotary shaker for 40 hours. The mycelium produced was collected by filtration, washed in sterile water and resuspended in 50 ml Mandels medium containing 0.1% glucose, 10 mM DTT plus 0.1% of either ferulic acid or eugenol to form two separate bioconversion mixtures. pH of the mixtures was 5.0.

TABLE 2

| Mixture No. | Reactant | Vanillin Conc. (ug/ml) 4 hrs | 75 hrs | 123 hrs |
|---|---|---|---|---|
| 1 | FA | 21.6 | 48.9 | 67.8 |
| 2 | EU | 6.1 | 9.1 | 13.9 |

The vanillin concentration continued to increase over the entire 123 hour incubation period.

EXAMPLE 3

This example shows the bioconversion of vanillin precursors in the presence of dithiothreitol using *Pseudomonas acidovorans* ATCC 15668.

*P. acidovorans* was inoculated with a loop into 100 ml of Mandels medium containing 1% of glucose and cultivated for 24 hrs on a rotary shaker at 30 degrees C. The cells so produced were isolated by centrifugation and were used to form 10 ml of a first bioconversion mixture containing Mandels medium (8 ml), 0.1% glucose, 0.1% FA and 10 mM DTT. A second bioconversion mixture was also formed in the same manner in which YNB medium and 10 mM succinate were substituted for Mandels medium and glucose. The mixtures were incubated at 25 degrees C. without aeration and vanillin concentration determined after different periods of time.

TABLE 3

| Mixture No. | pH | Vanillin Conc. (ug/ml) 1.5 hrs | 75 hrs | 123 hrs |
|---|---|---|---|---|
| 1 | 5.1 | 2.2 | 10.3 | 21.5 |

TABLE 3-continued

| Mixture No. | pH | Vanillin Conc. (ug/ml) 1.5 hrs | 75 hrs | 123 hrs |
|---|---|---|---|---|
| 2 | 7.0 | 1.1 | 5.9 | 8.7 |

It is seen that pH 5.1 is more favorable for vanillin formation than pH 7.0 when bioconversion is conducted with *P. acidovorans*.

EXAMPLE 4

This example shows bioconversion of ferulic acid by Pseudomonas putida in the presence of different sulfhydryl containing compounds.

*Pseudomonas putida* ATCC 55180 was inoculated into 100 ml fresh YNB medium containing 1% glucose. After culturing for 7 hours at 30 degrees C. with shaking at 250 rpm, the cells were collected and transferred into 200 ml of fresh YNB medium containing 1% glucose and cultured overnight on a rotary shaker at 30 degrees C. Cells were collected by centrifugation for 10 min. at 10,000 rpm and were used to form four different 10-ml bioconversion mixtures containing Mandels medium, 0.1% glucose and 0.1% FA. Each mixture contained a different sulfhydryl compound (concentration 10 mM) as shown in Table 4 below. The mixtures were incubated for varying periods of time and vanillin concentration determined.

TABLE 4

| Mixture No. | Sulfhydryl Compound | Vanillin Conc. (ug/ml) 1 hr | 100 hrs | 228 hrs |
|---|---|---|---|---|
| 1 | Beta-mercaptoethanol | 0.8 | 3.6 | 9.0 |
| 2 | DTE | 5.8 | 15.5 | 41.7 |
| 3 | DTT | 5.3 | 21.0 | 6.9 |

The results show that dithioerythritol and dithiothreitol were much more effective than beta-mercaptoethanol in promoting vanillin formation.

EXAMPLE 5

This example shows bench scale production and isolation of vanillin.

*Aspergillus niger* ATCC 11414 was inoculated into 200 ml Mandels medium containing 1% glucose and was cultured on a rotary shaker for 40 hrs at 30 degrees C. The mycelium from this first stage was isolated, inoculated into 500 ml Mandels medium (with 1% glucose) in a 1-liter bottle and was cultured under conditions identical to the first stage. The second stage culture was filtered and washed with Mandels medium to yield 250 ml mycelium. A bioconversion mixture was formed consisting of the washed mycelium, 750 ml of Mandels medium, 1 g glucose, 1 g FA, and enough DTT to bring the concentration to 10 mM.

The mixture was incubated at 30 degrees C. with minimal aeration. During the incubation period, glucose and DTT were added according to the schedule in Table 5. Vanillin concentration was as shown.

TABLE 5

| Time (hrs) | Addition | Vanillin Conc. (ug/ml) |
|---|---|---|
| 1 | 1.0 g glucose | 0.7 |
| 72 | 1.0 g glucose + DTT (10 mM) | 15.2 |
| 336 | DTT (5 mM) | 63.7 |
| 432 | None | 91.4 |

At 336 hrs, 360 ml of the bioconversion mixture was extracted three times with 120-ml portions of ethyl acetate, the extracts pooled and the ethyl acetate evaporated at 45 degrees C. under vacuum to yield a solid residue. The residue was dissolved in 10 ml 50% ethanol. Analysis showed that the residue contained 22 mg vanillin. The remaining bioconversion mixture (after 432 hrs incubation) was also processed in like manner to yield a solid residue-containing 58 mg of vanillin. A total of 80 mg vanillin was isolated in the two residues. Vanillin structure was confirmed by GC/MS and by HPLC analysis. The solid residues isolated contained other flavor components in addition to vanillin which contributed favorably to the overall sensory quality of the product.

A panel of certified flavorists described the product as creamy, sweet, buttery, custard, baked, and woody with a spicy undernote and egg-nog vanilla type flavor. The high quality product has application in a wide variety of foodstuffs such as dairy products, cakes, cookies, confectionary, etc.

EXAMPLE 6

The following example illustrates the use of yeast cells for bioconversion of ferulic acid to vanillin.

*Rhodotorula glutinis* ATCC 74056 was inoculated into 200 ml Mandels medium containing 1% glucose and was cultured at 30 degrees C. for 24 hours on a rotary shaker. In a second experiment, *Rhodotorula glutinis* ATCC 74056 cells were cultured in like manner for 240 hours. Cells were harvested by centrifugation at 10,000 rpm for 10 min., and washed with sterile Mandels medium. The washed cells were used to prepare bioconversion mixtures consisting of the cells, 100 ml Mandels medium, 0.1% glucose, 0.1% FA and 5 mM DTT. The bioconversion mixtures were incubated at 30 degrees C. without aeration. The vanillin concentration achieved with the 24-hr old (early stationary phase) cells was 85 ug/ml after 190 hrs incubation representing 8.5% conversion of ferulic acid to vanillin. Vanillin concentration with the 240-hr old (late stationary phase) cells in bioconversion conducted under the same conditions was only 45 ug/ml on the other hand illustration the superiority of early stationary phase cells for vanillin formation when *Rhodotorula glutinis* is used. Virtually no vanillin was formed in identical bioconversion conducted without DTT.

EXAMPLE 7

The following example illustrates the use of different sugars as assimilable carbon sources during the bioconversion step.

*Aspergillus niger* ATCC 11414 conidia were inoculated into 200 ml of Mandels medium containing 1% glucose and were cultured for 10 days on a rotary shaker at 200 rpm and 30 degrees C. Mycelium was aseptically collected by gravity filtration and washed with sterile Mandels medium without glucose. Equal portions of the mycelium were resuspended in 15 ml Mandels medium containing 0.1% of different sugars (e.g., glucose, galactose, sucrose, maltose, lactose, cellobiose, etc.), 0.1% FA, and 5 mM DTT. The mixtures were incubated at 25 degrees C. without shaking and analyzed for vanillin. All mixtures behaved similarly regardless of the type of sugar used yielding 17–21 ug/ml vanillin after 120 hrs incubation.

EXAMPLE 8

The following example shows the effects of DTT and glucose on the bioproduction of vanillin using *Corynebacterium glutamicum* cells.

Corynebacterium glutamicum ATCC 13032 cells were inoculated into MCGC medium containing 1% glucose at pH 7.0 and were cultured by shaking at 200 rpm for 5 days at 30 degrees C. One liter of the culture so produced was centrifuged and the cell pellet washed by resuspending in MCGC media and recentrifuging. The washed pellet was resuspended in 25 ml MCGC media and 6-ml portions inoculated into each of four 100-ml portions of MCGC medium containing 0.1% FA.

In addition, the bioconversion mixtures contained DTT and glucose as shown in Table 6 below. The mixtures were incubated with occasional stirring at 25 degrees C. and analyzed for the extent of conversion of ferulic acid to vanillin and vanillic acid.

TABLE 6

| Mixture No. | DTT (mM) | Glucose (%) | Conversion to Vanillin ug/ml | | Conversion to Vanillic Acid ug/ml | |
|---|---|---|---|---|---|---|
| | | | 24 hrs | 237 hrs | 24 hrs | 237 hrs |
| 1 | 0 | 0 | 7 | | 97 | |
| 2 | 1 | 0 | 10 | | 30 | |
| 3 | 0 | 1 | | 12 | | 8 |
| 4 | 1 | 1 | | 53 | | 18 |

The results show the requirement for the presence of a sulfhydryl compound and an assimilable carbon source in order to produce appreciable amounts of vanillin.

EXAMPLE 9

The following example shows the effect of concentration of different sulfhydryl compounds on vanillin production in the bioconversion of ferulic acid with *A. niger* cells.

*Aspergillus niger* ATCC 11414 was inoculated into 100-ml of Mandels medium containing 1% glucose in 250-ml flasks was grown for 6 days at 30 degrees C. with shaking at 200 rpm. Cells were harvested by gravity filtration and were washed with Mandels medium. One-ml portions of the cells were added to 50-ml test tubes containing 9 ml of Mandels medium having dissolved therein 0.1% ferulic acid, 0.1% glucose and different concentrations of sulfhydryl compound as shown in Table 7 below. The mixtures were incubated at 25 degrees C. with occasional shaking and the extent of vanillin production determined. The control contained all ingredients except a sulfhydryl compound.

TABLE 7

| Mix. No. | Sulfhydryl Compound | | Vanillin Concentration (ug/ml) | | | | | |
|---|---|---|---|---|---|---|---|---|
| | | | 2 hrs | 16 hrs | 40 hrs | 96 hrs | 120 hrs | 168 hrs |
| 1 | None | (control) | 0.03 | 0.02 | 0.02 | 0.38 | 0.36 | 3.41 |
| 2 | DTT | (5 mM) | 2.78 | 3.11 | 3.56 | 21.64 | 22.81 | 30.92 |
| 3 | | (10 mM) | 3.48 | 4.31 | 4.86 | 29.58 | 34.80 | 43.29 |
| 4 | | (20 mM) | 5.65 | 6.81 | 8.15 | 44.50 | 49.06 | 65.73 |
| 5 | Cys | (5 mM) | 1.16 | 1.58 | 1.44 | 3.41 | 4.01 | 4.96 |
| 6 | | (10 mM) | 3.37 | 3.96 | 4.32 | 17.38 | 6.73 | 2.02 |
| 7 | | (20 mM) | 2.31 | 7.52 | 8.34 | 31.57 | 11.84 | 5.64 |
| 8 | GSH | (5 mM) | 0.86 | 0.92 | 0.75 | 2.62 | 4.57 | 5.35 |
| 9 | | (10 mM) | 0.47 | 1.24 | 1.03 | 4.05 | 5.43 | 12.78 |
| 10 | | (20 mM) | 2.32 | 2.09 | 1.45 | 5.82 | 4.39 | 1.62 |

Vanillin production was greatest in those bioconversion mixtures conducted with DTT. Rate of production increased with DTT concentration. Bioconversions made with cysteine and glutathione showed maximum vanillin concentration at 96 hrs when present at the higher concentrations with lower vanillin concentration thereafter indicating the importance of controlling conversion time for maximizing vanillin production when metabolizable sulfhydryl compounds are utilized.

EXAMPLE 10

This Example demonstrates an improved yield of vanillin produced from callus cells of *V. fragrans* (previously known as *V. planifolia*) when a vanillin precursor and a sulfhydryl compound are incorporated into the medium. Vanilla tissue culture (undifferentiated callus cells) was prepared from *Vanilla fragrans* fruit placenta tissue following the generalized procedure set forth in U.S. Pat. Nos. 5,068,184 and 5,057,424, using Murashige and Skoog medium. Fruits of *Vanilla fragrans* were harvested from greenhouse-grown plants 41 days after pollination. Fruits were initially surface sterilized in 0.52% sodium hypochlorite for 4 min. Fruit end pieces approximately 2-cm long were removed and discarded. The remaining tissue was cut laterally into 2.5-cm pieces and further sterilized in 0.52% sodium hypochlorite for 3 min. and 70% ethyl alcohol for 1 min. The fruit pieces were rinsed 3 times with sterile deionized water and sliced longitudinally. The placentae containing ovules were removed and cut into 0.5 cm sections and placed into 100×15-mm plastic petri plates containing 25 ml of medium.

The medium consisted of Murashige and Skoog salts, 25 g/l sucrose, 2 mg/l glycine, 0.5 mg/l nicotinic acid, 0.1 mg/l pyridoxine hydrochloride, 3 mg/l 4-amino-3,5,6-trichloropicolinic acid, and 8 g/l Phytagar (GIBCO Laboratories, Grand Island, N.Y.). The medium, pH adjusted to 5.8, was autoclaved at 121° C.

Cultures were maintained at 25° C. with a 16 hour photoperiod. General Electric F40CW-RS-WM fluorescent tubes were used and produced approximately 98 umol/$m^2$s at the culture surface (21.5 cm). Explant cultures were transferred to fresh medium at 30-day intervals. Callus formation was observed from the placenta within 120 days of culture initiation. As the ovules developed into plantlets they were removed.

Sterile undifferentiated cells (1.1 g wet weight) were suspended in 5 ml of Murashige and Skoog Minimal Organics Medium without the incorporation of plant hormones. These suspended cells were added in 1 ml aliquots to five sterile flasks. Ferulic acid, glucose and DTT was added as stated in the Table 8 below.

TABLE 8

| | Composition of media in each flask. | | | |
|---|---|---|---|---|
| Flask # | Murashige Medium (ml) | Ferulic Acid (%) | Glucose (%) | DTT (mM) |
| 1 (Control) | 10 | 0 | 0 | 0 |
| 1 | 10 | 0.1 | 0 | 0 |
| 3 | 10 | 0.1 | 0.1 | 0 |
| 4 | 10 | 0.1 | 0.1 | 5 |
| 5 | 10 | 0 | 0 | 5 |

All transfers and manipulation were done under strictly sterile conditions. Cells were incubated at 30° C. with gentle mixing on a rotary shaker, 150 r.p.m.

The amounts of accumulated vanillin are set froth in Table 9 below.

TABLE 9

| | Vanillin accumulation over time. | | | | |
|---|---|---|---|---|---|
| | Vanillin (mg/L) Flask # | | | | |
| Time (hours) | 1 | 2 | 3 | 4 | 5 |
| 0 | 0 | 0 | 0 | 0 | 0 |
| 23 | 0.18 | 1.21 | 0.25 | 1.3 | 0.81 |
| 47 | 0.29 | 0.27 | 0.29 | 3.35 | 0.16 |
| 168 | 0.67 | 0.71 | 0.59 | 6.06 | 0.3 |

The results show the positive effect of DTT on vanillin formation when ferulic acid and glucose are present in the tissue culture suspension (flask #4) as compared to the control (flask #1) which was the tissue culture in medium alone and flasks #2 and 3 which were the tissue culture in medium with ferulic acid alone and ferulic acid with glucose respectively. Vinylguaiacol and vanillic acid were also detected as being produced in flasks #2, 3 and 4, all of which contained ferulic acid in the medium. The suspensions in flasks #1 and #5 contained small amounts of vanillic acid.

EXAMPLE 11

This Example demonstrates the improved production of vanillin when ferulic acid and DTT were added to culture media containing callus cell tissue cultures of *V. fragrans* at two separate pHs and synthetic medium compositions.

*V. fragrans* tissue culture was prepared in a similar manner as set forth in Example 10. Approximately 0.5 g wet weight of callus cells were added to each sterile flask. The compositions of the suspension in each of the flasks including the type of medium utilized and the pH of the suspension is reported below in Table 10.

TABLE 10

| | Composition of suspensions in each flask. | | | | |
|---|---|---|---|---|---|
| Flask # | Glucose (%) | Ferulic Acid (%) | DTT (mM) | Medium (5 ml) | pH |
| 1 | 0.1 | 0 | 0 | Mandels | 5.0 |
| 2 | 0.1 | 0 | 10 | Mandels | 5.0 |
| 3 | 0.1 | 0.1 | 10 | Mandels | 5.0 |
| 4 | 0.1 | 0 | 0 | MCGC | 6.0 |
| 5 | 0.1 | 0 | 10 | MCGC | 6.0 |
| 6 | 0.1 | 0.1 | 10 | MCGC | 6.0 |

In a similar manner as reported in Example 10, the vanillin accumulated in each flask suspension was measured over time. The results are reported below in Table 11.

TABLE 11

| | Vanillin formation over time. | | | | | |
|---|---|---|---|---|---|---|
| | Vanillin (mg/L) Flask # | | | | | |
| Time (hours) | 1 | 2 | 3 | 4 | 5 | 6 |
| 1 | 0.21 | 0 | 0.73 | 0.24 | 0.2 | 0.99 |
| 20 | 0.56 | 0.3 | 3.75 | 0.39 | 0.18 | 6.84 |
| 44 | 0.56 | 0.22 | 11.28 | 0.37 | 0.29 | 6.67 |
| 120 | 0.55 | 1.76 | 20.57 | 1.02 | 0.91 | 3.46 |

Significant increase of vanillin was detected in flasks #3 and #6 in which ferulic acid, glucose and DTT were present. Vanillic acid and vinylguaiacol were detected in the flasks #2, 3, 4, 5 and 6.

EXAMPLE 12

This Example demonstrates that vanillin can be produced by isolating enzymes from *V. fragrans* tissue culture (undifferentiated callus cells) and utilizing the enzymes in an in vitro enzymatic bioconversion of ferulic acid to vanillin with and without the incorporation of DTT.

Approximately 5 g wet weight of *V. fragrans* of callus culture derived from fruit placenta tissue as set forth in Example 10 was macerated with buffer for 2 hours at 4° C. Maceration buffer consisted of 50 mM citrate buffer, pH 5.0, 1.7M NaCl, 15 mM EDTA and 5 mM DTT. Two experiments were performed. In the first experiment, (flasks 7, 8 and 9) the tissue culture was sonicated (3 min. at 30 Hz) and then macerated for two hours. In the second experiment, the tissue culture was just macerated for two hours without sonication (flasks 1-6).

Macerate was centrifuged and filtered through Gelman filters (0.45 um) to remove particles. Filtrate was concentrated in a Centricon CON3 microconcentrator manufactured by Amicon USA (Amherst, MA) (3,000 Daltons cutoff). The samples were centrifuged at 4° C. for 60 min. at 9,000 r.p.m. (Sorvall RC-5B). This microconcentration step removed the majority of molecules smaller than 3,000 Daltons. An assumption was made that the enzymes which regulate the conversion of ferulic acid to vanillin should have a molecular weight exceeding 3,000 Daltons. Retentate was used as the crude enzymatic portion in the reaction mixtures described below.

Table 12 sets forth the compositional makeup of each of the flasks.

TABLE 12

| | Composition of suspensions. | | | |
|---|---|---|---|---|
| Flask # | Ferulic Acid 1% in ul | DTT 100 mM (ul) | Enzyme Preparation (ul) | Citrate Buffer 50 mM, pH5 (ul) |
| 1 | 100 | 100 | 200 | 600 |
| 2 | 0 | 0 | 200 | 800 |
| 3 | 100 | 100 | 200 | 600 |
| 4 | 0 | 0 | 200 | 800 |
| 5 | 100 | 100 | 200 | 600 |
| 6 | 0 | 0 | 200 | 800 |
| 7 | 0 | 0 | 100 | 250 |
| 8 | 33 | 0 | 100 | 250 |
| 9 | 33 | 33 | 100 | 250 |

The mixtures were incubated at 40° C. The amounts of vanillin produced over time are set forth in Table 13 below.

TABLE 13

| | Vanillin formation over time. | | | | | | | | |
|---|---|---|---|---|---|---|---|---|---|
| Time (hours) | Vanillin (mg/L) Flask # | | | | | | | | |
| | 1 | 2 | 3 | 4 | 5 | 6 | 7 | 8 | 9 |
| 0 | 0.3 | 0.3 | 1.9 | 2.0 | 0.7 | 0.2 | 0 | 0 | 0 |
| 28 | 2.2 | 0.7 | 40.5 | 2.9 | 28.3 | 1.8 | 2.6 | 2.2 | 6.2 |
| 48 | 13.3 | 1.1 | 44.8 | 2.5 | 45.13 | 1.3 | 5.2 | 3.1 | 8.3 |
| 120 | 55.2 | 0.6 | 44.1 | 2.4 | 57.1 | 1.4 | 5.7 | 5.6 | 14.4 |

In comparing the experimental runs utilizing enzymes from macerated tissue (flasks 1 to 6) it is clear that there was a marked improvement in vanillin production when ferulic acid and DTT were incorporated (flasks 1, 3 and 5) compared to the corresponding controls which did not incorporate ferulic acid and DTT (flasks 2, 4 and 6). Flasks 6-9 utilized an enzyme preparation derived from *V. fragrans* callus cells which was sonicated prior to maceration. Comparing these results, there appeared to be little difference when only ferulic acid was added (flask #8) and a large increase in vanillin production when ferulic acid and DTT were added (flask #9) when viewed against the control (flask #7).

We claim:

1. A process for the production of vanillin comprising contacting a bioconversion mixture comprised of an aqueous solution of a vanillin precursor present in a concentration in the range of between about 0.025% and 1.0% having the structural formula:

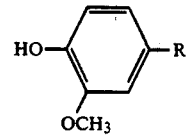

wherein R is selected from —CH=CH—COOH, —CH=CH$_2$, —CH$_2$—CH=CH$_2$, —CH=CH—CH$_2$OH, —CH=CH—CHO, —CH=CH—CH$_2$OH, —COOH, —CH=CH—CH$_3$,

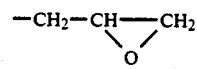

or —CH$_2$—CH(OH)—CH$_2$OH, with undifferentiated callus cells derived from a vanilla plant and/or enzymes obtained therefrom in the presence of a sulfhydryl compound selected from the group consisting of (a) HS—CH$_2$—(CH(OH))$_n$—CH$_2$—SH, where n is an integer of 1 to 4, (b) beta-mercaptoethanol, (c) mercaptoacetic acid and (d) sulfur containing amino acids and recovering vanillin.

2. The process according to claim 1 wherein the bioconversion mixture also contains an assimilable carbon source.

3. The process according to claim 2 wherein the assimilable carbon source is selected from the group consisting of glucose, fructose, maltose, sucrose and combinations thereof.

4. The process according to claim 1 wherein the vanillin precursor is selected from the group consisting of ferulic acid, eugenol, coniferyl alcohol and 4-vinylguaiacol.

5. The process according to claim 1 wherein the sulfhydryl compound is selected from the group consisting of dithiothreitol, dithioerythritol, glutathione, cysteine and combinations thereof.

6. The process according to claim 1 wherein the bioconversion mixture is maintained at a pH from about 3 to about 7 and at a temperature from about 20 degrees C. to about 40 degrees C.

7. The process according to claim 1 wherein the concentration of the sulfhydryl compound ranges from about 1 mM to about 100 mM.

8. The process according to claim 7 wherein the sulfhydryl concentration ranges from about 5 mM to about 20 mM.

9. The process according to claim 1 wherein the vanilla plant is selected from the group consisting of *V. fragrans, V. phaeantha, V. pompona* and *V. tahitensis.*

10. The process according to claim 1 wherein the callus cells are identified by ATCC #40354.

* * * * *